Figure 1:
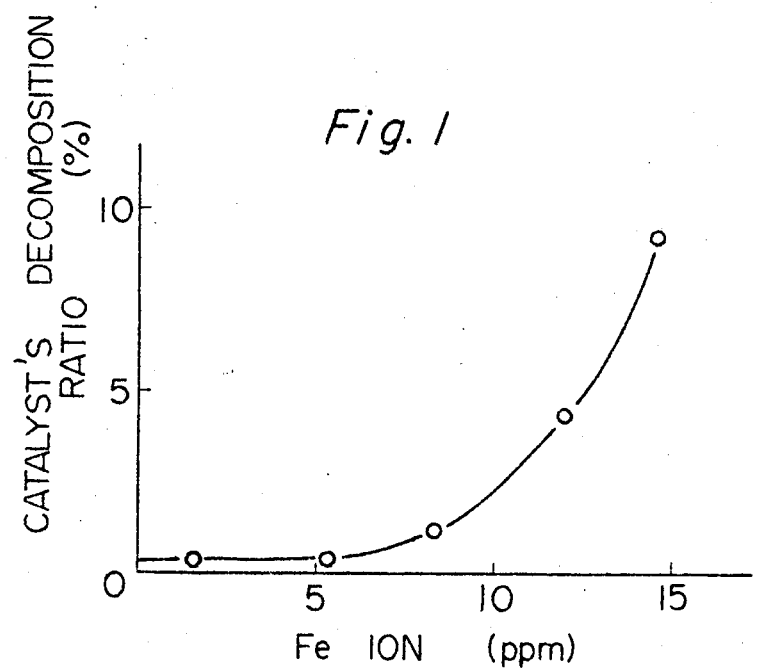

United States Patent [19]

Izumi et al.

[11] 3,996,298
[45] Dec. 7, 1976

[54] PROCESS FOR THE HYDRATION OF OLEFINS

[75] Inventors: Yusuke Izumi, Shinnanyo; Sumio Akiyama, Tokuyama; Kinya Yamazaki, Yono; Masato Todo; Takao Tomita, both of Tokuyama, all of Japan

[73] Assignee: Tokuyama Soda Kabushiki Kaisha, Japan

[22] Filed: Nov. 1, 1974

[21] Appl. No.: 520,094

Related U.S. Application Data

[63] Continuation of Ser. No. 238,129, March 27, 1972, abandoned.

[30] Foreign Application Priority Data

May 31, 1971 Japan .............................. 46-18720

[52] U.S. Cl. .......................... 260/641; 252/411 R
[51] Int. Cl.² ....................................... C07C 29/04
[58] Field of Search .................................. 260/641

[56] References Cited
UNITED STATES PATENTS

| | | | |
|---|---|---|---|
| 2,162,913 | 6/1939 | Eversole et al. | 260/641 |
| 2,173,187 | 9/1939 | Tanner | 260/641 |
| 2,579,601 | 12/1951 | Nelson et al. | 260/641 |
| 2,876,266 | 3/1959 | Wegner | 260/641 |
| 3,758,615 | 9/1973 | Izumi et al. | 260/641 |

FOREIGN PATENTS OR APPLICATIONS 486,783   6/1938   United Kingdom ............... 260/641

OTHER PUBLICATIONS

Kaiser et al., "I. & E.C. Product R & P", vol. 1, Dec. 1962, Reprint, pp. 296–301.

*Primary Examiner*—Joseph E. Evans
*Attorney, Agent, or Firm*—Sherman & Shalloway

[57] ABSTRACT

A process for the preparation of monohydric alcohols by contacting a monoolefin of 2–4 carbon atoms with an aqueous solution containing a heteropoly-acid ion, thereby subjecting the olefin to a hydration reaction, characterized in that said aqueous solution contains the heteropoly-acid ion in a concentration of at least 1/40,000 mol per liter and has a pH ranging from 2.0 to 4.5, and the aqueous solution is heated to a temperature sufficiently high for initiating the hydration reaction, while the free iron ion concentration therein is maintained at not higher than 10 ppm substantially throughout the whole hydration reaction period.

4 Claims, 2 Drawing Figures

PROCESS FOR THE HYDRATION OF OLEFINS

This is a continuation of application Ser. No. 238,129, filed Mar. 27, 1972 now abandoned.

This invention relates to a process for the hydration of olefins, which comprises hydrating an olefin by contacting it with an aqueous solution containing a heteropoly-acid ion as the catalyst, recovering alcohol from the resulting aqueous solution of the corresponding alcohol, and recycling the aqueous solution containing the heteropolyacid ion remaining after the removal of alcohol to the hydration step to use it again for the hydration of olefin.

A number of catalysts have been known as effective for direct hydration of olefins. Particularly, the utility of heteropoly-acid and water-soluble salts thereof for the hydration of olefin to produce alcohol and ether is known from British Pat. No. 487,384. More specifically, the heteropoly-acid includes borotungstic acid, phosphotungstic acid, silicotungstic acid, silicomolybdic acid, and phosphomolybdic acid. It is known that those heteropoly-acids generally exhibit olefin-hydrating activity also in the form of water-soluble salts thereof. To wit, heteropoly-acid in water is substantially dissociated into a hydrogen ion and a heteropoly-acid ion, similarly to ordinary mineral acid, and shows the catalytic activity for hydration of olefins as the result of the concurrent presence of the two types of ions.

Thus, in the hydration reaction of olefin, the heteropoly-acid ion acts as the main catalyst, while the hydrogen ion effectively acts as an activator of the former. For this reason, when a heteropoly-acid is used as the catalyst for hydration of olefin in the form of salt, a neutral salt exhibits only very minor catalytic activity, and therefore an acidic salt is advantageously employed. In other words, the concurrent presence of heteropoly-acid ions and hydrogen ions in the aqueous solution provides the advantageous catalyst system. As the typical metals for forming water-soluble, acidic salts of the heteropoly-acids, alkali metals such as sodium and potassium; and calcium, magnesium, cadmium and aluminum may be named.

According to the invention, the optimum results are obtained from the hydration of olefin using the heteropoly-acid, when the molar concentration of catalytic component range is 1/40,000 – 1/300, and the pH range is 2.0 – 4.5. The reaction is performed at 100 – 500 kg/cm$^2$, and at 150 – 370° C. The higher the molecular weight of the olefin, the lower may be the reaction temperature, within the above-specified range. For example, the temperature range of 200 – 350° C. is recommended for hydration of ethlene, while it is 200 – 300° C. for propylene, and 170 – 250° C. for butene.

The catalytic activity of those heteropoly-acid ions in the hydrating reaction of olefins thus being extremely high, we found that the durability of the activity is relatively short. For example, our experiments confirmed that in an iron reactor, 10% of the catalyst decomposed, under the reaction conditions of 300° C. and 150 kg/cm$^2$, within approximately 6 days.

We searched for the cause of such decrease of activity occurring with decomposition of the catalyst, etc., and discovered that the decrease in catalytic activity takes place when iron ions are substantially present in the reaction system for practicing the present invention, i.e., the aqueous solution containing heteropoly-acid ions. Thus we confirmed the necessity to avoid the substantial presence of free iron ions.

According to the invention, the catalyst system is composed of heteropoly-acid ions and hydrogen ions as already mentioned. For this reason the heteropoly-acid ion-containing aqueous solution is contacted with olefin at a pH ranging from 2.0 to 4.5. Such an acidic solution always dissolves iron or iron compounds as it contacts with the reactor, distillation system of the formed alcohol, transferring pipes, etc., and consequently unavoidably contains free iron ions at gradually increasing concentration. Furthermore, since the subject process concerns hydration, water must be added to the reaction system and, because the water itself contains iron ions although in minor quantities, from this source also iron ions gradually accumulate in the reaction system.

It is now found, according to the invention, that by substantially avoiding the concurrent presence of free iron with the catalyst ions composed chiefly of heteropoly-acid ions, the catalyst system can be used repetitively, without substantial reduction in the catalytic activity over prolonged periods of time.

It has previously been reported that iron silicotungstate, iron silicophosphate, ferric sulfate, ferric molybdate, etc. are used as catalysts for the hydration reaction of olefins (for example, Brennstoff-Chem. 38, 321 (1957), U.S. Patent 2.876,266). In view of this known information, it is quite unexpected that even a very small amount of iron ions abruptly reduces the catalytic activity of heteropoly-acid ions as described above.

Thus, according to the subject process for the preparation of monohydric alcohol which comprises contacting a monoolefin of 2 to 4 carbon atoms with an aqueous solution containing heteropoly-acid and thereby hydrating the olefin, the characteristic features residing in that the aqueous solution contains the heteropoly-acid ion at a concentration of at least 1/40,000 mol per liter and has a pH ranging from 2.0 to 4.5. Moreover, when the solution is heated to the temperature sufficiently high for initiating the hydration reaction, while the free iron ion concentration in the solution is maintained at not higher than 10 ppm substantially throughout the whole period of said reaction, monohydric alcohol corresponding to the starting olefin can be prepared with high conversion and high selectivity, without any substantial reduction in the catalyst's activity for a prolonged period.

The precise mechanism with which the free iron ion causes the decrease in catalytic activity is not yet clear. Our opinion is that either the catalyst ion and iron ion react to form practically inert, insoluble matter, or the iron ion acts catalytically to promote decomposition of the heteropoly-acid. Concerning the decrease in the catalytic activity which has been regarded as being caused by the catalyst's decomposition, it is confirmed that such decrease is not very appreciable after the first circulation of the catalyst solution in the flow reaction system, but upon repetitive recirculation of the solution, iron ions gradually accumulate in the solution to cause a marked reduction in the catalytic activity.

This can be clearly demonstrated by our experiments. For example, the correlation of the catalyst's decomposition ration (which is the reduction ratio and has substantially equivalent significance to the lowering ratio in the catalytic activity) with the concentration of concurrently existing iron ions is illustrated in FIG. 1, as to an aqueous solution of silicotungstic acid at 10$^{-3}$ mol/liter concentration, used at 290° C. and 150 kg/cm²G of propylene for 240 hours. As can be understood from FIG. 1, up to 5 ppm of iron ion concentration hardly interferes with the catalyst's activity, i.e., the catalyst's decomposition ratio is no more than 2% whereas the detrimental effect of the iron ion concentration becomes increasingly notable as it increases from 10 to 15 ppm. At 15 ppm, nearly 10% of the catalyst is decomposed and, beyond 15 ppm, the catalytic activity is decreased at such a rate as not to be industrially acceptable. Substantially the same tendency is recognized in the catalytic activities of other heteropoly-acid ions, e.g., borotungstic acid ions, phosphotungstic acid ions, silicompolybdic acid ions, and phosphomolybdic acid ions. Also the decomposition rate is substantially unaffected by pH variations in the solution within the acidic range. According to the present invention, therefore, the concentration of free iron ions in the catalytic aqueous solution to be supplied to, or caused to be present in, the hydration reaction system, through recirculation or other known means, is controlled to be not higher than 10 ppm and preferably below 5 ppm.

As sources of free iron ions which accumulate in the reaction system during the preparation of alcohol through the direct hydration of olefin, the following can be enumerated:

a. Elution from construction materials of the equipment employed, such as the reactor, distillation column, connecting pipes; etc., and b. Introduction from the water supply to the hydration reaction system, the former being the more significant.

Accordingly, in this invention the free iron ion concentration in the reaction system is controlled so as never to exceed 10 ppm, preferably 5 ppm, by preventing the entrance and accumulation of free iron ion in the reaction system through the routes (a) and (b) as much as possible, and if necessary (as in the majority of cases), by removing the iron ions unavoidably brought into the system and/or inactivating the same with, for example, a chelating agent.

As the means to advantageously practice the subject invention, for example, the following several embodiments can be employed, i. controlling the free iron ion concentration in the aqueous solution to keep it below 10 ppm, preferably below 5 ppm, by practicing the hydration reaction in a reactor of which at least the internal surfaces are constructed of non-ferrous metal which is non-corrosive to the aqueous solution.

As the non-ferrous metals useful for the above purpose, for example, nickel, chromium, titanium, zirconium, tantalum, silver, gold, and platinum may be named. It should be apparent that, while those non-ferrous metals may be used as the construction material of the reactor, lining or plating of the internal surfaces of the reactor with those metals is also effective. Thus, conventional ferrous reactors can be improved to be suited for use in the subject process, by lining or plating them with those non-ferrous metals. Also iron-containing alloys which hardly allow elution of iron ions can be used under certain circumstances.

Obviously, it is more desirable to construct not only the reactor, but also the distillation column for separating the formed alcohol and connecting pipes, from those non-ferrous metals. However, such will make the reaction apparatus extremely expensive. For this reason, in practice it is virtually impossible to completely prevent the entrance of free iron ions into the reaction system and, therefore, it is normally desirable, (probably excepting the case wherein very carefully refined, iron-free water is used), to concurrently practice the removal of free iron ions from the aqueous solution containing heteropoly-acid ions by the means later described, or by inactivation of the ion by chelation, etc.

ii. Controlling of the free iron ion concentration in the aqueous solution to be below 10 ppm, preferably below 5 ppm, substantially throughout the whole period of the specified hydration process, by contacting the heteropoly-acid ion-containing aqueous solution, which is obtained by separating the formed monohydric alcohol from the reaction mixture after completion of the hydration, with a cation exchanger, thereby adsorbing or removing by reaction the free iron ions contained in said solution, and recycling the aqueous solution to the hydration reaction system.

Exchangers suited for the removal of free iron ions in the aqueous solution, are cation exchange resins and inorganic cation exchangers. More specifically, cation exchange resins such as Amberlite (trademark, product of Rohm & Haas Co., U.S.A.), Diaion (trademark, product of MCI, Japan) and chelating cation exchangers which form chelate compounds with iron ions; and inorganic cation exchangers composed of phosphates of the metals of Group IV a of the periodic table; for example, are useful for this purpose.

The treatment of the aqueous solution with such cation exchangers can be effected by conventionally practiced ion-exchanging means, such as passing the above-specified heteropoly-acid ion-containing aqueous solution through a tower packed with the ion exchanger.

Figure 2:
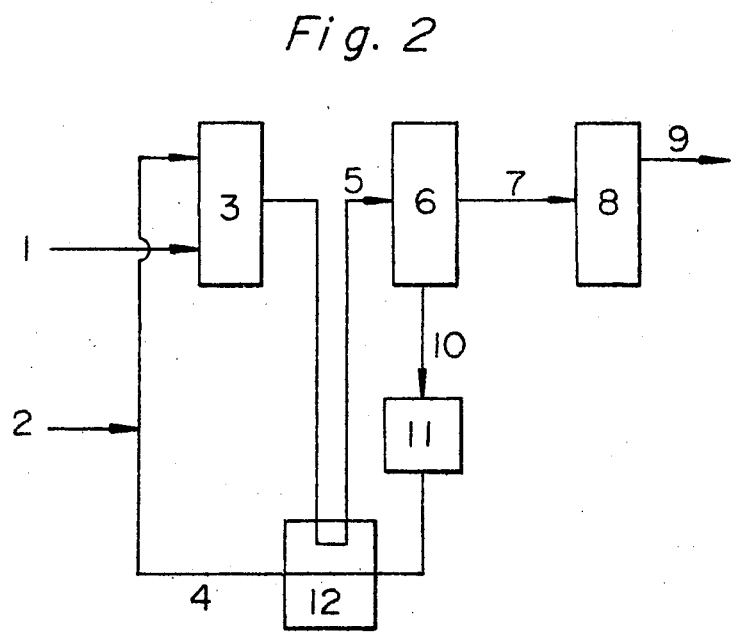

A typical embodiment of this method is shown as a flow chart in FIG. 2. Referring to said figure, the starting olefin is introduced into the reactor (3) through pipe (1), and the catalytic solution is supplied into the same reactor through pipe (4). The water replenishment to make up the water reduction due to its consumption during the hydration and from other minor causes, is effected from pipe (2). The reacted solution, i.e., a mixed aqueous solution of the reaction product and catalyst, is transferred through pipe (5), and exchanges heat with the recirculating catalytic solution at the heat exchanger (12). Then the solution is sent to the distillation column (6), to be separated into the desired product, i.e., alcohol, and the catalytic solution. The alcohol is further sent into the refining column (8) through pipe (7). The refined alcohol is withdrawn from pipe (9). The catalytic solution separated at the distillation column (6) is sent to the iron-removing column (11) packed with the ion exchanger, through pipe (10), to be removed of the free iron ion, and then recycled to the reactor (3) through pipe (4).

iii. Controlling of the free iron ion concentration in the aqueous solution to be not higher than 10 ppm, preferably below 5 ppm, substantially throughout the hydration reaction, by adding to the aqueous solution a stabilizer which can form a chelate compound with the free iron ion in situ.

Useful stabilizers are, for example, ortho-phosphoric acid, meta-phosphoric acid, pyrophosphoric acid, and polyphosphoric acid which can be expressed by the general formula, $P_2O_5 \cdot nH_2O$ (n stands for an integer); alkali metal salts thereof; ethylenediaminetetraacetic acid, nitrilotriacetic acid; and their water-soluble salts; etc. The stabilizers to be used in accordance with this embodiment are chelating agents which exhibit high reactivity with free iron ions, but show no detrimental effect on the olefinhydrating activity of the catalyst system composed chiefly of heteropoly-acid. Particularly preferred stabilizers are polyphosphoric acid in which the $P_2O_5$ content is no less than 72.4 wt. %, and water-soluble salts thereof with, for example, sodium and potassium. Normally the use of those stabilizers at purged from the autoclave, and the remaining catalytic solution containing the formed alcohol was let stand for 100 hours at 300° C. and 100 kg/cm² G, in the same container in the autoclave. Thereafter the reduction in silico-tungstic acid ion concentration in the solution was measured, with the results as shown in the last column of Table 1. The iron ion concentration in the solution after the reaction was 14 ppm when the stainless steel reactor was used, and in all other cases no more than 1 ppm.

Table 1

| Run No. | Construction Metal | Catalytic Solution SW Concentration (g/l) | pH | Reaction conditions Temp. (°C.) | Pres. (kg/cm²G) | Time (hr.) | Olefin | Main Product | Result Alcohol concentration (wt. %) | Selectivity (%) | SW Reduction Ratio (%/100 hrs.) |
| --- | --- | --- | --- | --- | --- | --- | --- | --- | --- | --- | --- |
| 1 (Control) | Stainless steel SUS27 | 3.0 | 3.0 | 230 | 200 | 1 | Propylene | Isopropanol | 8.6 | 99 | 4.8 |
| 2 | Ni | 3.0 | 3.0 | 230 | 200 | 1 | " | " | 8.7 | 99 | 1.2 |
| 3 | Ni | 1.0 | 2.8 | 230 | 200 | 1 | " | " | 10.7 | 98 | 0.3 |
| 4 | Cr | 3.0 | 3.0 | 230 | 200 | 1 | " | " | 8.8 | 99 | 0.8 |
| 5 | Ag | 3.0 | 3.0 | 230 | 200 | 1 | " | " | 8.6 | 99 | 1.0 |
| 6 | Ti | 3.0 | 3.0 | 230 | 200 | 1 | " | " | 8.7 | 99 | 0.8 |
| 7 | Zr | 3.0 | 3.0 | 230 | 200 | 1 | " | " | 8.8 | 99 | 1.2 |
| 8 | Ta | 3.0 | 3.0 | 230 | 200 | 1 | " | " | 8.8 | 99 | 0.8 |
| 9 | Au | 3.0 | 3.0 | 230 | 200 | 1 | " | " | 8.9 | 99 | 0.3 |
| 10 | Pt | 3.0 | 3.0 | 230 | 200 | 1 | " | " | 9.0 | 99 | 0.2 |
| 11 | Cr | 0.5 | 3.3 | 250 | 200 | 1 | " | " | 10.2 | 99 | 0.2 |
| 12 | Ti | 1.0 | 3.3 | 250 | 200 | 1 | Ethylene | Ethanol | 6.8 | 99 | 0.7 |
| 13 | Ti | 1.0 | 3.3 | 250 | 200 | 1 | Mixed butylene | Mixed butanol | 9.6 | 99 | 0.8 | the ratio of approximately 0.01 gram per liter of the solution is sufficient to achieve the desired effect. No correspondingly improved result can be expected from the addition of more than 1 gram of such a stabilizer per liter of the solution.

Only a few exemplary embodiments having been explained in the foregoing items(i) through (iii) as the specific means for reducing free iron ions in the catalytic solution, and it should be apparent that the scope of this invention is by no means limited thereto. Other means which are easily conceivable by those skilled in the art may, of course be employed. It is also preferable to practice two or more of those means concurrently, to maintain the free iron ion concentration in the catalytic solution at a still lowered level.

EXAMPLE

A container which was constructed of the metal specified in Table 1, second column, was charged with 150 ml of the catalytic solution containing silicotungstic acid ion (SW) at the concentration also specified in Table 1, and was inserted into a 500-ml capacity stainless steel autoclave. The specified olefin was introduced into the container under heating, until the temperature and pressure in the container reached the predetermined values, and hydrated for an hour. The results were as shown in the same table.

In order to determine the decomposition rate of the catalyst, after the reaction the unreacted olefin was

EXAMPLE 2

Catalytic solutions each containing silicotungstic acid (SWA), borotungstic acid (BWA), phosphotungstic acid (PWA), Silicomolybdic acid (SMA), or phosphomalybdic acid (PMA) at concentration of 3 g/liter were prepared, and their pH was adjusted to 2.8 — 3.0 with NaOH. In each run the catalytic solution was introduced into a silver-lined high pressure reactor from the upper part thereof, at a rate of 3 kg/hr. per 1 liter of the reactor's capacity. Simultaneously propylene was introduced into the same reactor from the bottom, at a rate of 0.26 kg/hr., to be continuously hydrated under the reaction conditions of 260° C. and 150 kg/cm²G. The reaction product was withdrawn from the bottom of the reactor together with the catalytic solution, which was subsequently separated by distillation. The separated catalytic solution was recirculated into the reactor. The reactor was continuously operated for 500 hours, but the iron ion concentration in the recirculated aqueous solution at no time exceeded 1 ppm. The average one-pass conversion, isopropanol concentration, space time yield (S.T.Y.) and isopropanol selectivity of the initial 24 hours, and of the last 24 hours, are shown in Table 2 below.

Table 2

| | Initial 24 Hours | | | | | Last 24 Hours | | | | |
| --- | --- | --- | --- | --- | --- | --- | --- | --- | --- | --- |
| | SWA | BWA | PWA | SMA | PMA | SWA | BWA | PWA | SMA | PMA |
| Conversion (%) | 67 | 64 | 66 | 68 | 67 | 67 | 64 | 65 | 67 | 56 |
| Concentration (wt.%) | 6.2 | 5.9 | 6.1 | 6.3 | 5.3 | 6.2 | 5.9 | 6.0 | 6.2 | 5.3 |
| S.T.Y.(kg/kg.cat.hr.) | 21.2 | 20.3 | 20.9 | 21.5 | 18.0 | 21.2 | 20.3 | 20.7 | 21.4 | 21.3 |
| Selectivity (%) | 98 | 99 | 98 | 98 | 99 | 98 | 99 | 98 | 98 | 99 |

The above results demonstrate that the average performance of the last 24 hour's operation is substantially the same as that of the initial 24 hours, as to all of the measurements.

Similar experiments were performed with titanium and zirconium reactors, and the results of 500 hours in FIG. 2 was not used), are also given as Runs 6 through 10.

Table 3

| | Run No. | Catalyst | Concentration of Catalytic Component (mol/liter) | Fe Concentration in Catalytic Solution (ppm) | Alcohol Yield (kg/hr) |
|---|---|---|---|---|---|
| Example | 1 | Silicotungstic acid | $2.0 \times 10^{-3}$ | 2 | 20.1 |
| | 2 | Borotungstic acid | $2.0 \times 10^{-3}$ | 2 | 20.1 |
| | 3 | Phosphotungstic acid | $1.8 \times 10^{-3}$ | 3 | 19.7 |
| | 4 | Silicomolybdic acid | $1.3 \times 10^{-3}$ | 2 | 17.6 |
| | 5 | Phosphomolybdic acid | $1.1 \times 10^{116\ a}$ | 4 | 16.0 |
| Control | 6 | Silicotungstic acid | $1.6 \times 10^{-3}$ | 14 | 16.6 |
| | 7 | Borotungstic acid | $1.4 \times 10^{-3}$ | 14 | 15.4 |
| | 8 | Phosphotungstic acid | $1.2 \times 10^{-3}$ | 16 | 14.2 |
| | 9 | Silicomolybdic acid | $7.1 \times 10^{-4}$ | 18 | 13.0 |
| | 10 | Phosphomolybdic acid | $6.5 \times 10^{-4}$ | 19 | 12.1 | continuous operation were found to be almost identical with those obtained with the silver-lined reactor. Furthermore, a gold-lined reactor was used in similar experiments, with substantially the same results.

In contrast thereto, when a stainless steel high pressure reactor was employed, the results of the reaction were substantially the same as those of the foregoing experiments during the initial period. However, after 500 hours of continuous operation, the silicotungstic acid ion concentration decreased by approximately 10%, and the S.T.Y. decreased by approximately 3%. The iron ion concentration in the solution at the end of the operation reached 18 ppm.

EXAMPLE 3

Propylene was hydrated through the procedures as illustrated in the flow chart of FIG. 2. The reactor and distillation column were made of stainless steel, with each having an inner diameter of 2 inches. The propylene was preheated and supplied into the reactor (3) through pipe (1), and water and catalyst were introduced through, respectively, pipes (2) and (4), at such rates that the pH of the catalytic solution became 2.8 – 3.0, and the concentration of the catalytic component became $2.1 \times 10^{-3}$ mol/liter. The reaction was continued for 720 hours, at 280° C. and 200 kg/cm$^2$G. The catalytic solution from which the reaction product was separated at the distillation column (6) was passed through a packed tower filled with cation exchange resin (trademark, Diaion PK 216) to be removed of free iron ions, then its pH was adjusted to between 2.8 – 3.0, and it was recirculated into the reactor. The concentration of the catalytic component in the solution and isopropanol yield in the reaction product after 720 hours of operation were as shown in Table 3.

For comparison, the results of the runs practiced simiarly, (except that the ion-removing column shown

EXAMPLE 4

The hydration in Run No. 2 of Table 3 (Example 3) was repeated except that the iron-removing column was packed with a chelating ion exchange resin (Chelate Resin CD 15, product of MCI). The results were identical with those of Run No. 2.

EXAMPLE 5

The catalyst stabilizers specified in Table 4 were added to the catalytic solutions containing silicotungstic acid ions (SW) at the specified concentrations, and to each of the catalyst systems isopropanol was added at a ratio of 6 wt. % to the total amount of the catalyst solution. The whole system was poured into a stainless steel autoclave, and allowed to stand for the predetermined period at 300° C. and 100 kg/cm$^2$. The resulting decrease in silicotungstic acid ions in each run is given in Table 4. In this Example, it was confirmed that the free iron ion concentration in the catalytic solution at the end of reaction was 10 ppm.

For comparison, the results of the runs in which no stabilizer was used are shown as Nos. 1 and 2 of Table 4.

Separately, 150 ml of the catalytic solution with the catalyst stabilizer similarly added was poured into a 500-ml capacity autoclave equipped with a stirrer, and into which olefin was added while the system was heated, until the predetermined temperature and pressure levels were attained. The hydration of olefin was then effected for each predetermined period. The results are shown in Table 5. Incidentally, the pH of catalytic solutions was adjusted with NaOH. In Table 5, Run No. 6 is an example in which the stabilizer was not added. It is seen from the results of Runs Nos. 1 – 6 that the stabilizers do not adversely affect the catalyst used in the invention.

Table 4

| | | Catalytic Solution | | | | |
|---|---|---|---|---|---|---|
| | | SW Concentration | Stabilizer | | | Decomposition |
| Run No. | Catalyst | (g/l) | Type | Concentration (g/l) | pH | (%/hr.) |
| 1 | Na$_2$H$_2$SW | 6.0 | — | — | 3.0 | 0.137 |
| 2 | NaH$_3$SW | 3.0 | — | — | 3.0 | 0.076 |
| 3 | Na$_2$H$_2$SW | 6.0 | Sodium metaphosphate | & 0.3 | 3.0 | 0.025 |
| 4 | " | 6.0 | Ortho-phosphoric acid | 0.3 | 3.0 | 0.00 |
| 5 | " | 6.0 | Sodium tripolyphosphate | 0.50 | 3.0 | 0.003 |
| 6 | " | 6.0 | Sodium tripolyphosphate | 0.05 | 3.0 | 0.040 |

Table 4-continued

| Run No. | Catalyst | Catalytic Solution SW Concentration (g/l) | Stabilizer Type | Concentration (g/l) | pH | Decomposition (%/hr.) |
|---|---|---|---|---|---|---|
| 7 | '' | 6.0 | EDTA-2K* | 0.2 | 3.0 | 0.054 |
| 8 | '' | 6.0 | NTA** | 0.2 | 3.0 | 0.060 |

Note
Run Nos. 1 and 2 are Controls.
*EDTA-2K stands for dipotassium salt of ethylene-diamine tetraacetic acid.
**NTA stands for nitrilotriacetic acid.

Table 5

| Run No. | Catalytic Solution SW Concentration (g/l) | Stabilizer Type | Concentration (g/l) | pH | Reaction Conditions Temp. (°C.) | Pressure (kg/cm²G) | Time (hr.) | Results Alcohol Concentration (wt. %) | Selectivity (%) |
|---|---|---|---|---|---|---|---|---|---|
| 1 | 3.0 | Sodium tri-polyphosphate | 0.3 | 3.0 | 230 | 200 | 1 | 8.0 | 99 |
| 2 | 6.0 | '' | 0.5 | 3.0 | 230 | 200 | 1 | 8.0 | 99 |
| 3 | 6.0 | '' | 0.05 | 3.0 | 230 | 200 | 1 | 11.5 | 99 |
| 4 | 6.0 | Ortho-phosphoric acid | 0.2 | 3.0 | 230 | 200 | 1 | 9.2 | 99 |
| 5 | 6.0 | EDTA | 0.25 | 3.0 | 230 | 200 | 1 | 8.0 | 99 |
| 6 | 6.0 | — | — | 3.0 | 230 | 200 | 1 | 8.0 | 99 |

EXAMPLE 6

The catalytic solution containing silicotungstic acid ions in a concentration of 6 g/liter, and either sodium tripolyphosphate or disodium ethylenediaminetetraacetate (EDTA-2NA) at the concentration specified in Table 6, and with the pH3.0 adjusted with NaOH, was introduced into a stainless steel, tubular high pressure reactor from the upper part thereof, at a rate of 3 kg/hr. per liter of the reactor's capacity. Simultaneously, propylene ($C'_3$) was intoduced into the reactor from the bottom part, at a rate of 0.26 kg/hr. Thus the continuous hydration of propylene was performed at 280° C. and 250 kg/cm²G. The reaction product was withdrawn from the bottom part of the reactor as a mixture of the catalyst aqueous solution with the product. Subsequently, the isopropanol produced was separated from the catalytic solution by distillation, the latter being recirculated into the reactor. The solution contained free iron ions at a concentration not higher than 8 ppm.

The average one-pass conversion of propylene, isopropanol (IPA) concentration, S.T.Y., and selectivity, of the initial 24 hours of operation were as shown in Table 6. The hydration was continued for 500 hours, without fresh supply of the catalytic solution. The average one-pass conversion of propylene, isopropanol concentration, S.T.Y., and selectivity after 500 hours of operation are also given in Table 6.

For comparison, the results of the run in which no catalyst stabilizer was added to the catalytic solution are concurrently given in Table 6 (Run No. 1).

From the same table, it is apparent that the catalyst stabilizers effectively promote the durability of the olefin-hydrating activity of the catalyst.

Table 6

| Run No. | Catalytic Solution Stabilizer Type | Concentration (g/l) | pH | Initial Period of Reaction $C'_3$ Conversion (%) | IPA Concentration (wt. %) | Selectivity (°C) | S.T.Y. (kg/kg.cat.hr.) | After 500 Hours Reaction $C'_3$ Conversion (%) | IPA Concentration (wt. %) | Selectivity (%) | S.T.Y. (kg/kg.cat.hr.) |
|---|---|---|---|---|---|---|---|---|---|---|---|
| 1 (Control) | — | — | 3.0 | 71 | 8.7 | 99 | 29.0 | 66 | 8.5 | 99 | 27.2 |
| 2 | Sodium tripolyphosphate | 0.2 | 3.0 | 70 | 8.6 | 99 | 28.7 | 69 | 8.6 | 99 | 28.7 |
| 3 | '' | 0.05 | 3.0 | 72 | 8.7 | 99 | 29.2 | 71 | 8.7 | 99 | 29.0 |
| 4 | EDTA-2Na | 0.25 | 3.0 | 70 | 8.5 | 99 | 28.6 | 70 | 8.5 | 99 | 28.5 |

EXAMPLE 7

Catalytic solutions each containing silicotungstic acid ions (SW) borotungstic acid ions (BW), phosphotungstic acid ions (PW) silicomolybdic acid ions (SM) or phosphomolybdic acid ions (PM) at in all cases a concentration of 3 g/liter, and 0.05 g/liter of ortho-phosphoric acid each had their pH adjusted to 3 – 3.3 with NaOH. Using the reactor employed in Example 6, the catalytic solution was introduced at a rate of 3 kg/hr. per liter of the reactor's capacity, and ethylene was introduced from the upper part of the reactor at a rate of 0.28 kg/hr. The liquid discharge was separated into the alcohol formed and the aqueous solution of catalyst, the latter being recirculated into the reactor as it was. The hydration reaction was continued for 500 hours, at 300° C. and 280 kg/cm²G. In this Example, ortho-phosphoric acid in an amount equivalent to that initially used was freshly added to the solution after 200 hours of operation. The free iron ion concentration in the solution was thus kept below 10 ppm throughout the continuous operation. The average ethylene conversion and selectivity for ethanol for the initial 8 hours of operation, and those of the last 8 hours, were as shown in Table 7. The results of the runs using no ortho-phosphoric acid are also given concurrently. In the Control runs, the iron ion concentration reached 18 – 20 ppm.

the formed monohydric alcohol, and treating said recovered heteropoly-acid ion-containing aqueous solution with a cation exchanger to separate and remove the free iron ions contained in said solution, and thereafter recycling said aqueous solution from which the free iron ions have been removed to the hydration reaction system.

Table 7

| | Initial 8 Hours | | | | Last 8 Hours | | | |
| | Conversion | | Selectivity | | Conversion | | Selectivity | |
| | Stabilizer | | Stabilizer | | Stabilizer | | Stabilizer | |
| Catalyst Ion | Added | Not Added | Added | Not Added | Added | Not Added | Added | Not Added |
| --- | --- | --- | --- | --- | --- | --- | --- | --- |
| SW | 62 | 62 | 99 | 99 | 61 | 53 | 99 | 99 |
| BW | 62 | 62 | 99 | 99 | 60 | 52 | 98 | 99 |
| PW | 58 | 57 | 99 | 99 | 56 | 47 | 98 | 99 |
| SM | 59 | 59 | 98 | 98 | 56 | 50 | 97 | 98 |
| PM | 56 | 55 | 98 | 98 | 54 | 41 | 98 | 98 |

We claim:

1. In a process for the preparation of monohydric alcohols by contacting a mono-olefin of 2-4 carbon atoms with an aqueous solution containing heteropoly-acid ions selected from the group consisting of borotungstic acid ions, phosphotungstic acid ions, silicotungstic acid ions, silicomolybdic acid ions and phosphomolybdic acid ions in a concentration of 1/40,000 to 1/300 mol per liter and at a pH ranging from 2.0 to 4.5 in the liquid phase at a pressure within the range of 100–500 Kg/cm$^2$G and at a temperature within the range of 150–370° C, thereby to subject the olefin to hydration reaction, the improvement comprising maintaining the free iron ion concentration of said aqueous solution at not higher than 10 ppm substantially throughout the whole hydration reaction period by performing said hydration reaction in a reaction vessel of which at least the internal surface is constructed of a metal selected from the group consisting of nickel, chromium, titanium, zirconium, tantalum, silver, gold and platinum.

2. In a process for the preparation of monohydric alcohols by contacting a mono-olefin of 2–4 carbon atoms with an aqueous solution containing heteropoly-acid ions selected from the group consisting of borotungstic acid ions, phosphotungstic acid ions, silicotungstic acid ions, silicomolybdic acid ions and phosphomolybdic acid ions in a concentration of 1/40,000 to 1/300 mol per liter and at a pH ranging from 2.0 to 4.5 in the liquid phase at a pressure within the range of 100–500 Kg/cm$^2$G and at a temperature within the range of 150–370° C, thereby to subject the olefin to hydration reaction, the improvement comprising maintaining the free iron ion concentration of said aqueous solution at not higher than 10 ppm substantially throughout the whole hydration reaction period by recovering the heteropoly-acid ion-containing aqueous solution from the reaction mixture containing the heteropoly-acid ion-containing aqueous solution and 3. In a process for the preparation of monohydric alcohols by contacting a mono-olefin of 2–4 carbon atoms with an aqueous solution containing heteropoly-acid ions selected from the group consisting of borotungstic acid ions, phosphotungstic acid ions, silicotungstic acid ions, silicomolybdic acid ions and phosphomolybdic acid ions in a concentration of 1/40,000 to 1/300 mol per liter and at a pH ranging from 2.0 to 4.5 in the liquid phase at a pressure within the range of 100–500 Kg/cm$^2$G and at a temperature within the range of 150–370° C, thereby to subject the olefin to hydration reaction, the improvement comprising maintaining the free iron ion concentration of said aqueous solution at not higher than 10 ppm substantially throughout the whole hydration reaction period by adding to said aqueous solution a stabilizer which can form a chelate compound with the free iron ions in said aqueous solution.

4. In a process for the preparation of monohydric alcohols by contacting a mono-olefin of 2–4 carbon atoms with an aqueous solution containing heteropoly-acid ions selected from the group consisting of borotungstic acid ions, phosphotungstic acid ions, silicontungstic acid ions, silicomolybdic acid ions and phosphomolybdic acid ions in a concentration of 1/40,000 to 1/300 mol per liter and at a pH ranging from 2.0 to 4.5 in the liquid phase at a pressure within the range of 100–500 Kg/cm$^2$G and at a temperature within the range of 150–370° C, thereby to subject the olefin to hydration reaction, the improvement comprising maintaining the free iron ion concentration of said aqueous solution at not higher than 10 ppm substantially throughout the whole hydration reaction period by performing the hydration reaction in a reactor of which at least the internal surfaces are composed of non-ferrous metal which is non-corrosive to said aqueous solution.

\* \* \* \* \*

UNITED STATES PATENT AND TRADEMARK OFFICE
CERTIFICATE OF CORRECTION

PATENT NO. : 3,996,298
DATED : December 7, 1976
INVENTOR(S) : IZUMI, ET AL.

It is certified that error appears in the above-identified patent and that said Letters Patent are hereby corrected as shown below:

Item 73, line 2, before "Japan" insert -- Yamaguchi-Ken --.

Signed and Sealed this

Fifth Day of April 1977

[SEAL]

Attest:

RUTH C. MASON
Attesting Officer

C. MARSHALL DANN
Commissioner of Patents and Trademarks